(12) United States Patent
Lee

(10) Patent No.: US 7,234,931 B2
(45) Date of Patent: Jun. 26, 2007

(54) FUNCTIONAL FOOD COMPOSITION HAVING EFFECTS OF RELIEVING ALCOHOL-INDUCED HANGOVER SYMPTOMS AND IMPROVING LIVER FUNCTION

(76) Inventor: Haeng Woo Lee, Daechi Samsung 2 Cha Apt. 403, 1014-1 Daechi 1-dong, Kangnam-gu, Seoul (KR) 135-968

( * ) Notice: Subject to any disclaimer, the term of this patent is extended or adjusted under 35 U.S.C. 154(b) by 369 days.

(21) Appl. No.: 11/007,883

(22) Filed: Dec. 9, 2004

(65) Prior Publication Data

US 2006/0045929 A1 Mar. 2, 2006

(30) Foreign Application Priority Data

Sep. 1, 2004 (KR) ...................... 10-2004-0069647

(51) Int. Cl.
*A61K 36/00* (2006.01)
*A61K 36/282* (2006.01)
*A61K 36/53* (2006.01)
*A61K 36/31* (2006.01)

(52) U.S. Cl. ...................... 425/725; 424/740; 424/747; 424/756

(58) Field of Classification Search ...................... None
See application file for complete search history.

(56) References Cited

U.S. PATENT DOCUMENTS

| | | | | |
|---|---|---|---|---|
| 4,618,495 A | * | 10/1986 | Okuda et al. ................ | 424/728 |
| 5,466,452 A | * | 11/1995 | Whittle ........................ | 424/750 |
| 2002/0031559 A1 | * | 3/2002 | Liang et al. ................. | 424/725 |
| 2003/0194451 A1 | * | 10/2003 | Cho et al. .................... | 424/728 |
| 2004/0161524 A1 | * | 8/2004 | Sakai et al. ................. | 426/655 |
| 2005/0147699 A1 | * | 7/2005 | Wu et al. .................... | 424/757 |
| 2005/0186293 A1 | * | 8/2005 | Santo et al. ................. | 424/736 |

FOREIGN PATENT DOCUMENTS

| | | | |
|---|---|---|---|
| CN | 1176814 | * | 3/1998 |
| JP | 06040931 | * | 2/1994 |
| JP | 2001247472 | * | 9/2001 |

* cited by examiner

*Primary Examiner*—Christopher R. Tate
(74) *Attorney, Agent, or Firm*—The Farrell Law Firm

(57) ABSTRACT

Disclosed is a functional food composition, which is effective in relieving alcohol-induced hangover symptoms and improving liver function. The composition includes 6–18% by dry weight of Polygonati Rhizoma, 10–40% by dry weight of *Astragalus membranaceus* Bge., 5–15% by dry weight of Artemisiae Scopariae Herba, 10–30% by dry weight of White Hoelen, 5–25% by dry weight of *Atractylodes* rhizome white, 4–12% by dry weight of Rehmanniae Radix, 2–10% by dry weight of *Mentha arvensis*, 2–10% by dry weight of *Curcuma longa*, and 2–10% by dry weight of Puerariae Radix, based on the total dry weight of the composition. The composition, including herbal components known to have no side effects, is effective in relieving hangover symptoms and improving liver function by removing or neutralizing factors responsible for hangover symptoms, such as alcohol absorbed in the body or acetaldehyde, the oxidation product of alcohol.

10 Claims, No Drawings

FUNCTIONAL FOOD COMPOSITION HAVING EFFECTS OF RELIEVING ALCOHOL-INDUCED HANGOVER SYMPTOMS AND IMPROVING LIVER FUNCTION

PRIORITY

This application claims priority to an application entitled "Functional Food Compositions Having the Effect On Eliminating an Alcoholic Hangover And Improvement Of Liver Function" filed in Korean Intellectual Property Office on Sept. 1, 2004 and assigned Ser. No. 2004-69647, the contents of which are incorporated herein by reference.

BACKGROUND OF THE INVENTION

1. Field of the Invention

The present invention, in general, relates to a functional food composition for relieving alcohol-induced hangover symptoms and improving liver function. More particularly, the present invention relates to a functional food composition, which is capable of relieving alcohol-induced hangover symptoms by removing or neutralizing a factor responsible for hangover symptoms, such as alcohol (ethanol) absorbed in the body or acetaldehyde, the oxidation product of alcohol, which is a harmful toxin affecting the liver and other organs, as well as basically improving liver function.

2. Description of the Prior Art

The liver is the body's largest organ that performs a variety of functions including metabolizing various nutrients required in the body, producing energy needed in the brain, and binding to toxic substances and detoxifing them. The functions of liver further include secreting bile salt to help degrade and absorb fatty acids, storing the remaining carbohydrates and vitamins, synthesizing blood proteins, and synthesizing cholesterol as a component of the plasma membrane. When the liver, having such various functions, is damaged, several symptoms such as jaundice and anemia occur.

Frequent or excessive alcohol drinking causes alcoholic fatty liver, or more seriously alcoholic hepatitis or most seriously alcoholic cirrhosis, which occurs in about 10–35% of drinkers. In some cases, without the early-stage alcoholic fatty liver or middle-stage hepatitis, the end-stage cirrhosis may occur initially and lead to death.

Alcohol is typically oxidized to carbon dioxide and water by about three pathways: the first pathway involving alcohol dehydrogenase (ADH), present in the gastrointestinal tract or liver; the second pathway involving the microsomal ethanol oxidizing system located in the endoplasmic reticulum; and the third pathway involving catalase located in the peroxysomes.

Typically, when a suitable amount of alcohol is consumed, the aforementioned oxidation systems perform their functions fully, thereby not showing undesired symptoms due to alcohol. However, too much alcohol destroys the balance of the metabolic system and thus disrupts internal homeostasis. In this situation, the liver is most greatly damaged, thereby causing several long-term liver dysfunctions, such as fatty liver and cirrhosis, and short-term symptoms including headache, reduced concentration, stomach pain and defective digestion. Typically, "hangover" indicates the short-term symptoms, but in a broad sense, includes such short-term symptoms occurring the day following excessive drinking and long-term symptoms such as liver dysfunctions.

In Korea, various foods, for example, bean sprouts, dried pollacks and mung beans, have been used to relieve hangover symptoms for a long time. In particular, bean sprouts have high-content asparaginic acid that protects the liver by stimulating ADH to oxidize alcohol. Asparaginic acid-containing beverages for relieving hangover symptoms are also commercially available.

Foods for protecting liver function comprising mung beans are disclosed in Korean Pat. Laid-open Publication Nos. 1998-076168 and 1997-000075. Also, a beverage for relieving hangover symptoms comprising pears and raisin tree is disclosed in Korean Pat. Application No. 1999-56964. A natural tea for relieving hangover symptoms comprising extracts of red alder and *Sorbus commixta* is disclosed in Korean Pat. Registration No. 181168.

Despite many efforts for relieving alcohol-induced hangover symptoms, satisfactory results have not been achieved with respect to the development of therapeutic agents or beverages capable of effectively relieving or reducing hangover symptoms. In particular, since conventional beverages for relieving hangovers only revive the central nervous system depressed by alcohol intake, they have a problem of not neutralizing toxins or not improving or protecting liver function.

SUMMARY OF THE INVENTION

Accordingly, the present invention aims to provide a functional food composition having excellent ability to relieve alcohol-induced hangover symptoms by removing or neutralizing a factor responsible for hangover symptoms, such as alcohol (ethanol) absorbed in the body or acetaldehyde as the oxidation product of alcohol, which is a harmful toxin affecting the liver and other organs, and to improve liver function.

DETAILED DESCRIPTION OF THE INVENTION

In accordance with the present invention, there is provided a functional food composition able to relieve alcohol-induced hangover symptoms and improving liver function, comprising 6–18% by dry weight of Polygonati Rhizoma, 10–40% by dry weight of *Astragalus membranaceus* Bge., 5–15% by dry weight of Artemisiae Scopariae Herba, 10–30% by dry weight of White Hoelen, 5–25% by dry weight of *Atractylodes* rhizome white, 4-12% by dry weight of Rehmanniae Radix, 2–10% by dry weight of *Mentha arvensis,* 2-10% by dry weight of *Curcuma longa*, and 2-10% by dry weight of Puerariae Radix, based on the total dry weight of the composition.

Leading to the present invention, the intensive and thorough research into the ability of various combinations of medical herbs to relieve hangover symptoms, with an aim to develop a functional food effective in relieving hangover symptoms using medical herbs, resulted in the finding that a composition composed of about ten medical herbs has an effect of relieving hangover symptoms and improving liver function.

The novel composition according to the present invention may be used as a functional food for relieving hangover symptoms and improving liver function.

The present composition is prepared with a basic combination or preferred combinations of medical herbs, as follows.

Basal Combination of Medical Herbs

The functional food composition of the present invention comprises 6–18% by dry weight of Polygonati Rhizoma, 10–40% by dry weight of *Astragalus membranaceus* Bge., 5–15% by dry weight of Artemisiae Scopariae Herba, 10–30% by dry weight of White Hoelen, 5–25% by dry weight of *Atractylodes* rhizome white, 4–12% by dry weight of Rehmanniae Radix, 2–10% by dry weight of *Mentha arvensis*, 2–10% by dry weight of *Curcuma longa*, and 2–10% by dry weight of Puerariae Radix, based on the total dry weight of the composition.

Preferably, the present composition may further comprise 0–45% by dry weight of Salviae Miltiorrhizae Radix, 0–45% by dry weight of *Codonopsis pilosula* NANNF, and 0–20% by dry weight of Amydae Carapax, based on the total dry weight of the composition.

More preferably, the present composition, based on the total dry weight of the composition, comprises 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix and 25–35% by dry weight of Salviae Miltiorrhizae Radix, or 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix, 25–35% by dry weight of Salviae Miltiorrhizae Radix and 5–15% by dry weight of Amydae Carapax, or 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix, 15–25% by dry weight of *Codonopsis pilosula* NANNF and 5–15% by dry weight of Amydae Carapax.

The present composition is prepared to have effects of relieving hangover symptoms and improving liver function with no severe adverse effects by making a suitable combination of several medical herbs to strengthen liver functions based on Chinese medicine.

To accomplish the above object, the present invention employs Polygonati Rhizoma, *Astragalus membranaceus* Bge., Artemisiae Scopariae Herba, White Hoelen, *Atractylodes* rhizome white, Rehmanniae Radix, *Mentha arvensis*, *Curcuma longa*, Puerariae Radix, Amydae Carapax, Salviae Miltiorrhizae Radix, and *Codonopsis pilosula* NANNF. These medical herbs will be described in detail, as follows.

Polygonati Rhizoma, which is one of the essential components of the present composition, is a wonder medicine strengthening bone and muscle according to the Korean oriental medicine guideline "Dong-Eui-Bo-Gam". In particular, it is known to have an aphrodisiac effect of increasing sexual capacity of males and treating frigidity of females. Also, it strengthens the digestive functions of the spleen and stomach and stimulates appetite, and has antitussive, antihypertensive and blood sugar-lowering effects. Further, it suppresses fat deposition in the liver.

*Astragalus membranaceus* Bge., which is one of the essential components of the present composition, is a perennial plant belonging to the Leguminosae family, and its roots are used for therapy purposes. It contains fomononetin, betain, cholin, isoliquiritigenin, amino acids, saponin and isoflavone. It has various pharmaceutical effects including protecting the liver, stimulating immune responses, strengthening the heart and stimulating urination (Chinese medicine encyclopedia, p121, published by the Shanghai Science Technology Press, Tokyo, 1985). Also, according to Korean Pat. Application Nos. 1994-040125 and 1999-010284, *Astragalus membranaceus* Bge. stimulates immune functions, has a therapeutic effect on hepatitis caused by carbon tetrachloride and has an antihypersive effect by virtue of its diuretic action. In particular, isoflavone extracted from *Astragalus membranaceus* Bge. has an excellent effect on protecting the liver. According to the Korean oriental medicine guideline "Dong-Eui-Bo-Gam", *Astragalus membranaceus* Bge. improves the condition of the skin, lowers blood pressure, prevents the formation of pus and has hematic and tonic effects, and especially, has an excellent effect on invigorating weakly individuals or individuals suffering from excessive sweating.

Artemisiae Scopariae Herba (or Herba artmesiae capillaries), which is one of the essential components of the present composition, is abundant in nutrients, active components, vitamins and minerals, all of which activate the liver function weakened by alcohol intake, smoking, excessive work, stress, frequent drinking and administration of various medicines. It also improves the liver function, excretes toxic waste materials in the body, thus cleaning the liver, and strengthens the detoxification function of the liver, thus improving fat metabolism. Due to these effects, Artemisiae Scopariae Herba is effective in relieving fatigue and improving physical strength.

White Hoelen, which is one of the essential components of the present composition, strengthens the spleen, has a sedative effect, relieves congenital fever, and makes the body warm up. It is also effective on digestive ulcers, muscle spasm, thirst, vertigo, psychological stress and insomnia. Due to its tonic, diuretic and sedative effects, White Hoelen is used as an oriental medicine for treating kidney-associated diseases, cystitis and urethritis. White Hoelen inhibits irritant dermatitis, and has been used as a tonic for a long time. It also protects the spleen, reduces phlegm and tranquilizes the mind. According to the results of pharmacological tests, White Hoelen has diuretic, blood sugar-lowering and sedative effects, as well as having an effect of reviving the immune system. Also, White Hoelen is used for treating vomiting, ascites, diarrhea, amnesia and sleep disorders. White Hoelen is known to have excellent effects on the stomach, liver, spleen and kidney, and is used as an oriental medicine for treating individuals weakened due to diseases or suffering from chronic gastroenteric troubles. White Hoelen is also known to have therapeutic efficacy on gonorrhea in men and women, other sexually transmitted diseases and women's diseases.

*Atractylodes* rhizome white, which is one of the essential components of the present composition, has diuretic and diaphoretic effects against disturbance of the water metabolism in digestive organs and subcutaneous tissues, and has therapeutic efficacy on acute pain, gastroenteritis and dropsy. As a folk remedy, *Atractylodes* rhizome white is used as an antihypertensive agent, and is used to treat the loss of appetite due to weak stomach and watery feces with a yellow face.

Rehmanniae Radix, which is one of the essential components of the present composition, is prepared from the roots of *Rehmannia glutinosa*. Rehmanniae Radix has been divided into three types according to its processing: fresh, dried, and steamed, which are called in Korea "Saeng-Ji-Whang", "Gun-Ji-Whang" and "Sook-Ji-Whang", respectively. Steamed Rehmanniae Radix is used as a hematic and used for treating menstrual cycle disorder, constitutional weakness, retarded growth of children, dementia, premature ejaculation and impotence. Fresh Rehmanniae Radix is used for treating constitutional weakness, hematemesis, nose bleeding, uterine hemorrhage, menstrual cycle disorder and constipation. Dried Rehmanniae Radix has therapeutic efficacy on extensive thirst in febrile diseases and polydipsia caused by intestinal fever, and is effective in stopping hematemesis and nose bleeding. Also, dried Rehmanniae Radix strengthens the physiological functions of the kidney and revives the sprit and energy, thus preventing or treating gray hair.

*Mentha arvensis*, which is one of the essential components of the present composition, contains 1-menthol, 1-limone isomenthone, camphene and 1-menthol-β-D-glucoside. It has various effects of expanding capillary blood vessels in the skin, alleviating fever, stimulating vasorelaxation, cleaning the stomach, and inhibiting viral activity. Also, it has anti-inflammatory, analgesic, stomachic, tonic and choleretic effects, and is effective in improving appetite and relieving fatigue.

*Curcuma longa*, which is one of the essential components of the present composition, was consumed as "the loyal house tea" only in loyal houses of China, Japan, the Choseon dynasty of Korea and Europe. According to the Korean herbal medicine guideline "Dong-Eui-Bo-Gam" and the Chinese herbal medicine guide line "Bon-Cho-Gang-Mok", *Curcuma longa* has excellent effects of stimulating the detoxification function of the liver, increasing bile secretion and nourishing the blood.

Puerariae Radix, which is one of the essential components of the present composition, promotes sweating by relaxing the pores of the skin, alleviates fever, headache and neck stiffness, eliminates thirst, and is effective on the fluttering of the legs and arms due to chest oppression and uneasiness in febrile diseases and polydipsia. Also, it is used upon long-term diarrhea leading to utter exhaustion due to weak digestive organs. A Puerariae Radix decoction has a significant antihypertensive effect. An ethanol extract of Puerariae Radix has an effect of alleviating fever, and Puerariae Radix powder has an effect of dilating blood vessels in the skin.

Amydae Carapax, which is one of the essential components of the present composition, according to the results of the research entitled "the inhibition of liver fibrosis by Amydae Carapax pills", inhibits inflammation and thus decreases transformation and necrosis of hepatocytes, resulting in prevention of fibrosis of the liver tissue.

Salviae Miltiorrhizae Radix, as a component of the present composition, improves blood circulation thereby eliminating blood stasis and alleviating joint pains in the limbs. Salviae Miltiorrhizae Radix is used for treating menstrual cycle disorder, menstrual pains and postpartum abdominal pains, as well as acute pain in the chest and abdomen and bruises. Also, Salviae Miltiorrhizae Radix is used for treating mental confusion due to high fever, delirious utterances, chest oppression, insomnia, skin irritation, and tongue redness. Further, Salviae Miltiorrhizae Radix is used for treating rashes resulting from inflammation of the skin, and has therapeutic efficacy on the early stage of breast cancer due to its effect of vitalizing and nourishing the blood. Due to its relaxing effect, Salviae Miltiorrhizae Radix is used for treating chest oppression, insomnia and palpitation. Salviae Miltiorrhizae Radix has the following pharmaceutical effects: it dilates the coronary arteries and thus significantly promotes blood flow; it activates lipid metabolism and thus reduces blood chloresterol; and it has antihypertensive, liver function-improving, sedative, anti-inflammatory, anticancer and antibacterial effects.

*Codonopsis pilosula* NANNF, as a component of the present composition, is a perennial herb belonging to the Companulaceae family, and contains vitamin B, saponin, sucrose, glucose, inulin, starch and a viscous substance. *Codonopsis pilosula* NANNF has expectorant, tonic and stomachic effects, and is used for treating chronic wasting diseases, chronic respiratory diseases, anemia and chronic gastroenteritis. Also, *Codonopsis pilosula* NANNF has a relaxing effect and is effective on chlorosis (anemia characterized by a sallow and yellow face), pulmonary tuberculosis and leukemia. In particular, *Codonopsis pilosula* NANNF has been reported to contain a relatively high content of steroid glycoside, and to have tonic, expectorant, antihypertensive and antibacterial effects and effects of improving the body's resistance to pathogens and increasing erythrocytes and hemoglobin levels. Also, *Codonopsis pilosula* NANNF strengthens the lung, spleen and stomach and nourishes blood, thereby strengthening the liver.

In addition, the present composition may further comprise a concentrated extract of jujube, honey or an oak pyroligneous liquid. Preferably, the concentrated extract of jujube, honey and oak pyroligneous liquid may be contained in amounts of 10–200 parts by weight, 10–200 parts by weight and 5–50 parts by weight, respectively, based on 100 parts by weight of the composition.

Jujube, as a component of the present composition, contains sugars (43%) as a major ingredient, proteins (1.5%), lipids (0.8%), ash (4.2%) and vitamins (60 mg %). Jujube seeds contain betulin and betulic acid. Also, jujube contains an amount of cAMP 1000-fold higher than other plants, and also contains sugars and organic acids. Jujube is used in the Chinese medical field as a diuretic, a tonic and a relaxation agent. Also, Jujube is known to have sedative effects on insomnia and oversensitiveness and antitumor and antiallergic effects.

Honey, as a component of the present composition, contains high amounts of fructose and glucose (70%), sucrose, maltose, and organic acids, and acts in the lung, spleen and large intestine. Honey strengthens the spleen, stomach and lung, has antitussive, antidotal and analgesic effects, and facilitates the evacuation of feces. Also, honey increases the body's resistance to pathogens, promotes wound healing, inhibits bacterial activity, and relieves fatigue and hangover symptoms.

Oak pyroligneous liquid (CHAM-HYANG, food additive) as a component of the present composition, which is also known as pyroligneous acid or wood vinegar, has anticancer, antimutation, alcohol-detoxifying and antioxidant effects.

The novel composition for relieving alcohol-induced hangover symptoms and improving liver function according to the present invention may be prepared as follow.

The aforementioned herbal components are finely ground, mixed at the ratios as described above, and extracted with a 5–10-fold volume of water at 100–200° C. for 3–5 hours to provide a concentrated herbal extract. First, the herbal components are washed with distilled water to completely remove impurities, dried and finely ground to give powders.

The obtained powders are extracted with a solvent to provide an extract. If desired, to increase the yield, the extraction may be repeated twice or more. Remaining herbal powders and the solvent are removed from the extract by separation and concentration, for example, using a centrifugal separator and rotatory evaporation concentrator.

The concentrated herbal extract is supplemented with 10–200 parts by weight of a concentrated extract of jujube, 10–200 parts by weight of honey and 5–50 parts by weight of an oak pyroligneous liquid, based on 100 parts by weight of the concentrated herbal extract.

The present composition for relieving alcohol-induced hangover symptoms and improving liver function is preferably administred orally. Solid preparations for oral administration include tablets, pills, powders, granules and capsules, and may include one or more excipients, which are exemplified by starch, calcium carbonate, sucrose and lactose, magnesium stearate such as gelatin, and a lubricant such as talc. Liquid preparations for oral administration include suspensions, content solutions, emulsions and syrups, and may include simple diluents, such as water and liquid paraffin, and various excipients, which are exemplified by humectants, sweeteners, aromatics and preservatives.

A better understanding of the present invention may be obtained through the following examples which are set forth to illustrate, but are not to be construed as the limit of the present invention.

EXAMPLE 1

Preparation of Beverage for Improving Liver Function and Relieving Hangover Symptoms First Process Each medical herb was washed with potable water and finely ground using a grinder. After being ground, 120 g of Polygonati Rhizoma, 250 g of *Astragalus membranaceus* Bge., 100 g of Artemisiae Scopariae Herba, 200 g of White Hoelen, 150 g of *Atractylodes* rhizome white, 80 g of Rehmanniae Radix, 60 g of *Mentha arvensis*, 60 g of *Curcuma longa*, and 60 g of Puerariae Radix were put into a round flask, and extracted with 1 L of distilled water at 90–100° C. for 3 hours. Then, the extract was filtered at room temperature, centrifuged to remove remaining herbal powders, and concentrated using a rotary evaporation concentrator.

Second Process 60 g of the concentrated extract was mixed with 58 g of a concentrated extract of jujube, 62 g of honey and 6 g of an oak pyroligneous liquid, thus producing a beverage for improving liver function and relieving hangover symptoms.

EXAMPLE 2

Preparation of Beverage for Improving Liver Function and Relieving Hangover Symptoms Containing Salviae Miltiorrhizae Radix and Amydae Carapax First Process Each medical herb was washed with edible water and finely ground using a grinder. After being ground, 120 g of Polygonati Rhizoma, 100 g of Artemisiae Scopariae Herba, 80 g of Rehmanniae Radix, 250 g of *Astragalus membranaceus* Bge., 200 g of White Hoelen, 300 g of Salviae Miltiorrhizae Radix, 100 g of *Atractylodes* rhizome white, 100 g of Amydae Carapax, 60 g of *Mentha arvensis*, 60 g of *Curcuma longa*, and 60 g of Puerariae Radix were put into a round flask, and extracted with 1 L of distilled water at 90–100° C. for 3 hours. Then, the extract was filtered at room temperature, centrifuged to remove remaining herbal powders, and concentrated using a rotary evaporation concentrator.

Second Process 60 g of the concentrated extract was mixed with 58 g of a concentrated extract of jujube, 62 g of honey and 6 g of an oak pyroligneous liquid, thus producing a beverage for improving liver function and relieving hangover symptoms.

EXAMPLE 3

Preparation of Beverage for Improving Liver Function and Relieving Hangover Symptoms Containing *Codonopsis pilosula* NANNF and Amydae Carapax A beverage for improving liver function and relieving hangover symptoms was prepared according to the same procedure as in Example 2 except for the use of *Codonopsis pilosula* NANNF instead of Salviae Miltiorrhizae Radix.

EXAMPLE 4

Evaluation of the Effect of the Present Beverage Compositions on Blood Alcohol Concentrations To determine whether the present beverage compositions have an effect of relieving hangover symptoms, blood alcohol concentrations were measured in rats administered with the beverage compositions. Thirty male Sprague-Dawley white rats with an initial weight of 180–200 g were divided into three groups. The rats were adjusted to a new environment at 25±1° C. for over one week, and were orally administered with each of the beverage compositions prepared in Examples 1, 2 and 3 in a dose of 700 mg/kg using a stainless steel zoned. Extracts of alder tree and Acanthopanacis Cortex, which have been known to have an effect of relieving hangover symptoms, were used as comparative groups 1 and 2, respectively. After one hour, the rats were orally administered with 3 ml/kg of 40% ethanol. One hour and four hours after the administration of 40% ethanol, blood was collected from tail veins of the rats, and centrifuged at 3000 rpm for 10 min. The supernatants were recovered, and blood alcohol concentrations were measured using an ethanol assay kit (Sigma #332-A, USA). The blood alcohol concentrations were calculated according to the procedure supplied by the Sigma Company and the following Equation 1.

Alcohol Conc. (mg/ml)=(Absorbance of test group/Absorbance of control group)×100    [Equation 1]

The results are given in Table 1, below. The blood alcohol concentrations were measured in ten rats for each group, and the result for each group was expressed as mean±SD.

TABLE 1

|  | After 1 hr | After 4 hr |
|---|---|---|
| Control | 0.124 ± 0.015 | 0.119 ± 0.015 |
| E. 1 | 0.057 ± 0.008 | 0.041 ± 0.004 |
| E. 2 | 0.045 ± 0.005 | 0.033 ± 0.008 |
| E. 3 | 0.064 ± 0.006 | 0.049 ± 0.005 |

TABLE 1-continued

|  | After 1 hr | After 4 hr |
|---|---|---|
| C.E. 1 | 0.071 ± 0.009 | 0.059 ± 0.012 |
| C.E. 2 | 0.082 ± 0.011 | 0.077 ± 0.003 |

As apparent from the data of Table 1, the present beverage compositions were found to inhibit alcohol absorbance by the body and thus effectively reduce blood alcohol concentratons. The three beverage compositions all displayed this effect, but the beverage composition prepared in Example 1 was most effective.

EXAMPLE 5

Sensory Test

The beverage composition prepared in Example 1 was orally administered to subjects before or after drinking. The subjects answered written questions about their hangover symptoms. The results are given in Table 2, below.

TABLE 2

|  |  | Before drinking (15 subjects) | | After drinking (12 subjects) | |
|---|---|---|---|---|---|
| Headache | No headache | 15 | 100% | 12 | 100% |
| Stomach pain | No change No pain | 13 | 87% | 10 | 83% |
|  | No change | 2 | 13% | 1 | 8% |
|  | Worsen |  |  | 1 | 8% |
| Feces odor | Less odor | 15 | 100% | 11 | 92% |
|  | No change |  |  | 1 | 8% |
| Physical condition | Better | 13 | 87% | 12 | 100% |
|  | No change | 2 | 13% |  |  |

As shown in Table 2, the subjects displayed improvement in about two symptoms. Also, in excessive drinkers among the subjects, the hangover symptoms were relieved more.

In addition, to individuals suffering from headache and stomach pain after alcohol consumption, the beverage composition prepared in Example 1 was administered orally the day after alcohol intake. After one and two hours, hangover symptoms were evaluated, and the results are given in Table 3.

TABLE 3

|  |  | 1 hr after ingestion of the composition | 2 hr after ingestion of the composition |
|---|---|---|---|
| Group suffering from headache (six subjects) | No headache | 5 | 5 |
|  | No change | 1 | 1 |
| Group suffering from stomach pain (six subjects) | No pain | 4 | 6 |
|  | No change |  |  |
|  | Slight pain | 2 |  |
| Physical condition | Better | 10 | 11 |
|  | No change | 1 |  |

As shown in Table 3, the present composition was found to have excellent effect in relieving hangover symptoms when administered before or after alcohol consumption.

EXAMPLE 6

Evaluation of the Effect of the Present Beverage Composition on the Detoxification Function of the Liver in Rats Male Sprague-Dawley white rats with an initial weight of 180–200 g were divided into five groups (a normal group, a control group, a test group and two comparative groups), which each consist of eight rats. Extracts of alder tree and Acanthopanacis Cortex, which have been known to have an effect of relieving hangover symptoms, were used as comparative groups 1 and 2, respectively. The rats were grouped so that each group had a similar average weight. The rats were adjusted to a new environment in a breeding room under a 12:12 hr light-dark cycle at 22±5° C. for over one week, wherein each rat was place in a different stainless steel cage.

Once everyday for one week, the control group was orally administered with 5 ml/kg weight of physiological saline (0.9% NaCl), and the test and comparative groups were orally administered with 200 ml/kg weight of the present beverage composition. To induce hepatotoxidity (all groups were starved for 16 hrs before the hepatotoxicity induction), three hours after the final administration, the normal group was intraperitoneally administered with 3 ml/kg weight of olive oil, and the control and test groups were intraperitoneally administered with 3 ml/kg weight of a mixture of CC14 and olive oil (1:1). 24 hrs after the hepatotoxicity induction, in all groups, serum ALT (alanine aminotransferase) activity and AST (aspartate aminotransferase) activity were measured. The results are given in Table 4, below.

TABLE 4

|  | ALT (karmen/ml) | AST (karmen/ml) |
|---|---|---|
| Normal group | 16.42 ± 0.38 | 150.37 ± 4.75 |
| Control group | 274.41 ± 1.47 | 484.56 ± 4.84 |
| Test group | 207.94 ± 3.71 | 427.36 ± 5.48 |
| C.E. 1 | 237.87 ± 2.74 | 453.67 ± 1.53 |
| C.E. 2 | 241.32 ± 1.27 | 447.39 ± 2.55 |

As shown in Table 4, groups administered with the present composition exhibited a significant decrease in ALT and AST activity in comparison with the control group. These lower ALT and AST activities than the control group were believed to result from the levels of aminotransferase functioning to remove toxic amino groups from the liver being reduced, and the liver thus being recovered to normal states. These results indicate that the present composition has potential to improve the liver function.

EXAMPLE 7

Clinical Test for the Effect of the Present Beverage Compositions on the Liver Function 100 ml of the beverage composition for improving liver function and relieving hangover symptoms, prepared in Example 1, was orally administered to twenty male patients aged 45 to 50 with abnormal liver function three times per day for 40 days. Before, during and after the administration of the composition, parameters of liver function, GPT, GOT and γ-GTP levels were measured, and the results are given in Table 5, below. Typically, normal ranges of GPT, GOT and γ-GTP levels are 5–40, 10–40 and 0–60, respectively.

TABLE 5

|  | Before administration | After 20 days | After 40 days |
|---|---|---|---|
| GPT (U/L) | 118 | 54 | 35 |
| GOT (U/L) | 78 | 42 | 30 |
| γ-GTP (U/L) | 92 | 77 | 47 |

As shown in Table 5, when the patients with abnormal liver function were administered with the present composition for 40 days, GPT, GOT and γ-GTP levels were remarkably lowered. These results indicate that the present composition has effects of improving liver function and preventing liver diseases.

As described hereinbefore, the present composition reduces the alcohol absorbance of the body. Thus, when administered before or after alcohol consumption, the present composition can protect the liver and improve the liver function, as well as reduce hangover symptoms.

What is claimed is:

1. A functional food composition, which is effective in relieving alcohol-induced hangover symptoms and improving liver function, the functional food composition comprising 6–18% by dry weight of Polygonati Rhizoma, 10–40% by dry weight of *Astragalus membranaceus* Bge., 5–15% by dry weight of Artemisiae Scopariae Herba, 10–30% by dry weight of White Hoelen, 5–25% by dry weight of *Atractylodes* rhizome white, 4–12% by dry weight of Rehmanniae Radix, 2–10% by dry weight of *Mentha arvensis*, 2–10% by dry weight of *Curcuma longa*, and 2–10% by dry weight of Puerariae Radix, based on the total dry weight of the composition.

2. The functional food composition as set forth in claim 1, further comprising 0–45% by dry weight of Salviae Miltiorrhizae Radix, 0–45% by dry weight of *Codonopsis pilosula* NANNF, and 0–20% by dry weight of Amydae Carapax, based on the total dry weight of the composition.

3. The functional food composition as set forth in claim 2, comprising 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix and 25–35% by dry weight of Salviae Miltiorrhizae Radix, based on the total dry weight of the composition.

4. The functional food composition as set forth in claim 2, comprising 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix, 25–35% by dry weight of Salviae Miltiorrhizae Radix and 5–15% by dry weight of Amydae Carapax, based on the total dry weight of the composition.

5. The functional food composition as set forth in claim 2, comprising 9–15% by dry weight of Polygonati Rhizoma, 20–30% by dry weight of *Astragalus membranaceus* Bge., 8–12% by dry weight of Artemisiae Scopariae Herba, 15–25% by dry weight of White Hoelen, 5–15% by dry weight of *Atractylodes* rhizome white, 6–10% by dry weight of Rehmanniae Radix, 4–8% by dry weight of *Mentha arvensis*, 4–8% by dry weight of *Curcuma longa*, 4–8% by dry weight of Puerariae Radix, 15–25% by dry weight of *Codonopsis pilosula* NANNF and 5–15% by dry weight of Amydae Carapax, based on the total dry weight of the composition.

6. The functional food composition as set forth in claims 1, wherein the composition is formulated into tablets, capsules, pills, granules, or a liquid preparation.

7. The functional food composition as set forth in claim 2, wherein the composition is formulated into tablets, capsules, pills, granules, or a liquid preparation.

8. The functional food composition as set forth in claim 3, wherein the composition is formulated into tablets, capsules, pills, granules, or a liquid preparation.

9. The functional food composition as set forth in claim 4, wherein the composition is formulated into tablets, capsules, pills, granules, or a liquid preparation.

10. The functional food composition as set forth in claim 5, wherein the composition is formulated into tablets, capsules, pills, granules, or a liquid preparation.

* * * * *